(12) United States Patent
Wanker et al.

(10) Patent No.: US 8,974,768 B2
(45) Date of Patent: Mar. 10, 2015

(54) AZO COMPOUNDS REDUCING FORMATION AND TOXICITY OF AMYLOID BETA AGGREGATION INTERMEDIATES

(75) Inventors: Erich Wanker, Berlin (DE); Thomas Wiglenda, Berlin (DE); Julius Tachu Babila, Berlin (DE); Annett Boeddrich, Falkensee (DE); Michael Schmidt, Berlin (DE); Franziska Schiele, Rottenburg-Kiebingen (DE)

(73) Assignee: Max-Delbrueck-Centrum fuer Molekulare Medizin, Berlin (DE)

( * ) Notice: Subject to any disclaimer, the term of this patent is extended or adjusted under 35 U.S.C. 154(b) by 0 days.

(21) Appl. No.: 13/636,831

(22) PCT Filed: Mar. 23, 2011

(86) PCT No.: PCT/EP2011/054462
§ 371 (c)(1),
(2), (4) Date: Dec. 14, 2012

(87) PCT Pub. No.: WO2011/117305
PCT Pub. Date: Sep. 29, 2011

(65) Prior Publication Data
US 2013/0078186 A1    Mar. 28, 2013

(30) Foreign Application Priority Data

Mar. 23, 2010  (EP) ................................. 10157378

(51) Int. Cl.
| *A61K 31/655* | (2006.01) |
| *A61K 49/10* | (2006.01) |
| *C07C 245/06* | (2006.01) |
| *C07C 245/18* | (2006.01) |
| *C07C 245/20* | (2006.01) |
| *C07C 245/08* | (2006.01) |
| *C07C 245/10* | (2006.01) |
| *C07C 309/46* | (2006.01) |
| *C07C 309/49* | (2006.01) |
| *C07C 309/50* | (2006.01) |
| *C07C 331/28* | (2006.01) |
| *C07D 213/76* | (2006.01) |
| *C07D 249/14* | (2006.01) |
| *C07D 277/50* | (2006.01) |
| *C07C 245/24* | (2006.01) |

(52) U.S. Cl.
CPC ............. *C07C 245/08* (2013.01); *A61K 31/655* (2013.01); *C07C 245/10* (2013.01); *C07C 309/46* (2013.01); *C07C 309/49* (2013.01); *C07C 309/50* (2013.01); *C07C 331/28* (2013.01); *C07D 213/76* (2013.01); *C07D 249/14* (2013.01); *C07D 277/50* (2013.01); *C07C 245/24* (2013.01)
USPC ............ 424/9.1; 514/150; 534/843; 534/780; 534/721

(58) Field of Classification Search
USPC ......................................................... 424/9.1
See application file for complete search history.

(56) References Cited

U.S. PATENT DOCUMENTS

| 5,382,691 A | * | 1/1995 | Stern et al. ..................... 564/415 |
| 5,633,407 A | * | 5/1997 | Stern et al. ..................... 564/415 |
| 6,020,374 A | | 2/2000 | Geier et al. |
| 6,218,506 B1 | | 4/2001 | Krafft et al. |
| 2003/0203495 A1 | | 10/2003 | Rupp |
| 2005/0065062 A1 | | 3/2005 | Roscoe et al. |
| 2006/0252844 A1 | | 11/2006 | Mentak |
| 2007/0032458 A1 | | 2/2007 | Suh et al. |
| 2007/0207509 A1 | | 9/2007 | Frederickson et al. |
| 2010/0178203 A1 | | 7/2010 | Kane |

FOREIGN PATENT DOCUMENTS

| EP | 1266884 A1 | 12/2002 |
| EP | 1571158 A2 | 9/2005 |
| EP | 0998495 B1 | 12/2006 |
| EP | 1808444 A1 | 7/2007 |
| WO | 9716194 A1 | 5/1997 |
| WO | 9924394 A2 | 5/1999 |
| WO | 0130979 A1 | 5/2001 |
| WO | 02080855 A2 | 10/2002 |
| WO | 03051374 A2 | 6/2003 |
| WO | 2004044241 A2 | 5/2004 |
| WO | 2004055175 A1 | 7/2004 |
| WO | 2004076640 A2 | 9/2004 |
| WO | 2009084982 A1 | 7/2009 |

OTHER PUBLICATIONS

Hawley's Condensed Chemical Dictionary (11th Ed., Sax, N. I. and Lewis, R. J. (editors), Van Nostrand Reinhold Co. (NY), 1987, p. 302.*
Das et al. Food and Chemical Toxicology, 1997, 35, 835-838.*
Byrn et al., Chapter 11 Hydrates and Solvates in Solid-State Chemistry of Drugs (2d Ed. 1999), 233-247.*
Grant & Hackh's Chemical Dictionary (5th ed. 1987) (p. 542).*

(Continued)

*Primary Examiner* — Brandon Fetterolf
*Assistant Examiner* — Ana Z Muresan
(74) *Attorney, Agent, or Firm* — Rothwell, Figg, Ernst & Manbeck, P.C.

(57) ABSTRACT

The present invention relates to compounds suitable as modulators of protein misfolding and/or protein aggregation. The compounds are particularly suitable as inhibitors of amyloid aggregate formation and/or modulators of amyloid surface properties, and/or as activators of degradation or reduction of amyloid aggregates.

20 Claims, 7 Drawing Sheets

(56) References Cited

OTHER PUBLICATIONS

Figure 1:
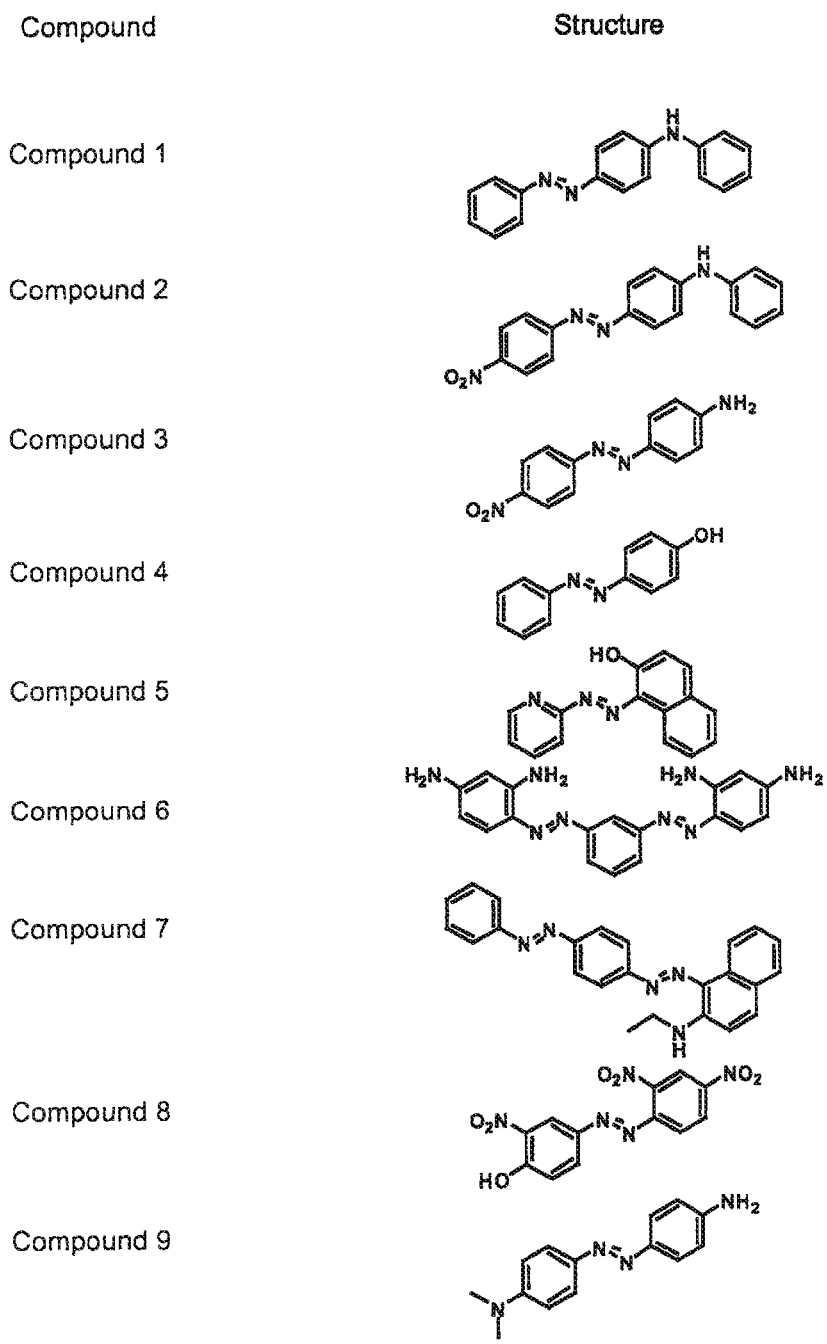
Figure 1:
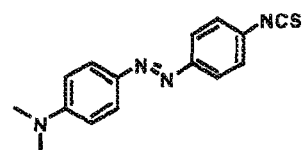
Figure 1:
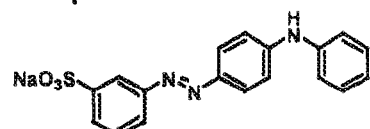
Figure 1:
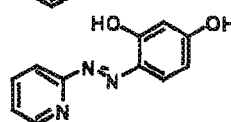
Figure 1:
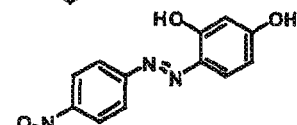
Figure 1:
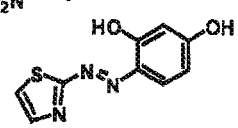
Figure 1:
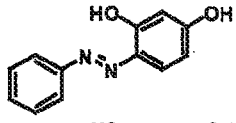
Figure 1:
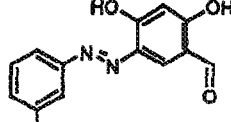
Figure 1:
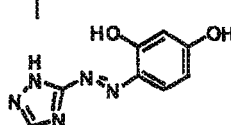
Figure 1:
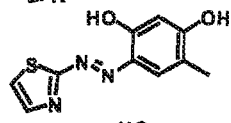
Figure 1:
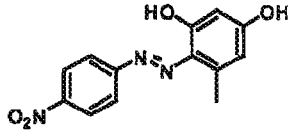
Figure 1:
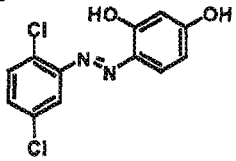
Figure 1:
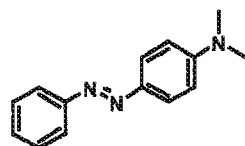
Figure 1:
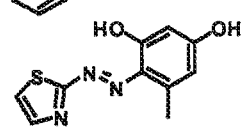
Figure 1:
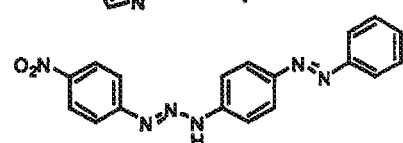
Figure 1:
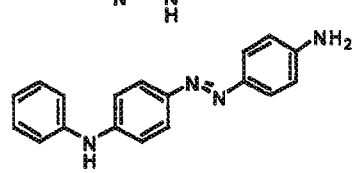
Figure 1:
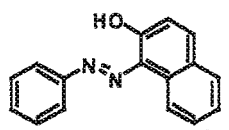
Figure 1:
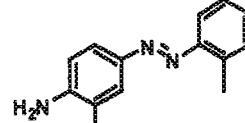
Figure 1:
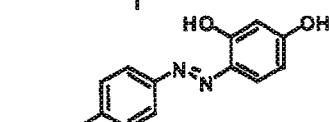
Figure 1:
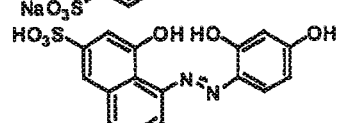
Figure 1:
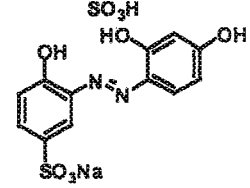
Figure 1:
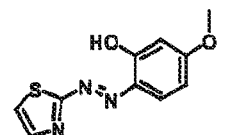
Figure 1:
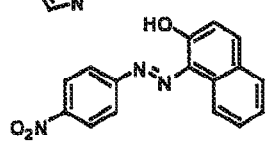
Figure 1:
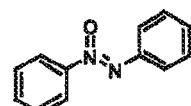
Figure 1:
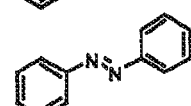
Figure 1:
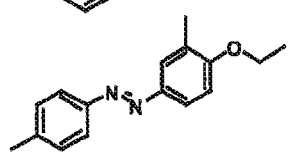
Figure 1:
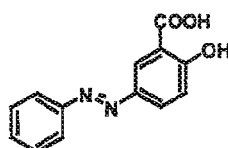
Figure 1:
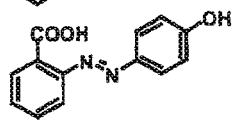
Figure 1:
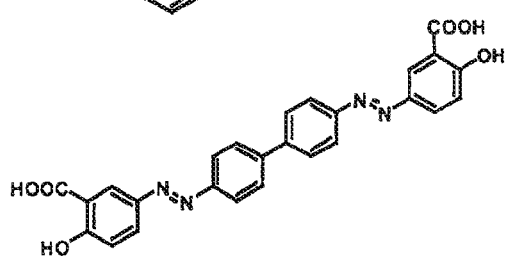

Doh-ura et al. Cellular and Molecular Neurobiology, vol. 27, No. 3, May 2007 p. 303-316.*
Jiao et al. Journal of Cellular Biochemistry (2008), 105(6), 1399-1409.*
Dolphin Gunnar T et al: "Designed amyloid beta peptide fibril—a tool for high-throughput screening of fibril inhibitors" CHEMMEDCHEM, vol. 2, No. 11, Nov. 2007, pp. 1613-1623.
K. Taniguchi S et al: "Inhibitation of heparin-induced tau filament formation by phenothiazines, polyphenols and porphyrins" Journal of Biological Chemistry, American Society for Biochemistry and Molecular Biology, Inc, US LNKD DOI:10.1074/JBC.M408714200, vol. 280, No. 9, Mar. 4, 2005, pp. 7614-7623.
Masuda Masami et al: "Small molecule inhibitors of alpha-synuclein filament assembly" Biochemistry, vol. 45, No. 19, May 2006, pp. 6085-6094.
Rudyk H et al: "Synthesis and evaluation of analogues of congo red as potential compounds against transmissible spongiform encephalopathies" European Journal of Medicinal Chemistry, Editions Scientifique Elsevier, Paris, FR LNKD—DOI:10.1016/S0223-5234(03)00081-3, vol. 38, No. 6, Jun. 1, 2003 pp. 567-579.
Chiti et al., "Protein Misfolding, Functional Amyloid, and Human Disease", Annu. Rev. Biochem, 2006, 75, pp. 333-366.
Partial European Search Report issued on Jul. 8, 2010 for European Priority Application EP 10 157 378.0, 8 pgs.
International Preliminary Report on Patentability issued on Sep. 25, 2012 for International Application PCT/EP2011/054462, 10 pgs.
Sutani et al, "Stimulus responsive drug release from polymer gel. Controlled release of ionic drug from polyampholyte gel", Radiation Physics and Chemistry, 64 (2002), pp. 331-336.
Office Action in European Application No. 11 709 731.1-1453 dated Jun. 19, 2014, 11 pgs.

* cited by examiner

Compound 10

Compound 11

Compound 12

Compound 13

Compound 14

Compound 15

Compound 16

Compound 17

Compound 18

Compound 19

Compound 20

Compound 21

Compound 22

Compound 23

Compound 24

Compound 25

Compound 26

Compound 27

Compound 28

Compound 29

Compound 30

Compound 31

Comparative Compounds

| Comparative Compound | Structure |
|---|---|
| Compound 32 | 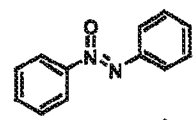 |
| Compound 33 | 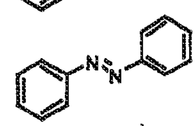 |
| Compound 34 | 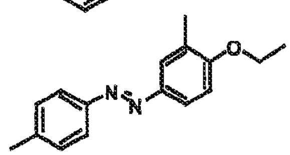 |
| Compound A |  |
| Compound B |  |
| Compound C |  |

A)

B)

C)

AZO COMPOUNDS REDUCING FORMATION AND TOXICITY OF AMYLOID BETA AGGREGATION INTERMEDIATES

CROSS REFERENCE TO RELATED APPLICATION

This application is a 35 U.S.C. 371 National Phase Entry Application from PCT/EP2011/054462, filed Mar. 23, 2011, which claims the benefit of European Patent Application No. 10157378.0 filed on Mar. 23, 2010, the disclosure of which is incorporated herein in its entirety by reference.

The present invention relates to compounds suitable as modulators of protein misfolding and/or protein aggregation. The compounds are particularly suitable as inhibitors of amyloid aggregate formation and/or as modulators of amyloid surface properties and/or as activators of degradation or reduction of amyloid aggregates.

Alzheimer's disease is a progressive neurodegenerative illness characterized by memory loss and other cognitive deficits. It is associated with distinct pathologies, including the formation of aggregates, the primary protein component of which is amyloid-β.

WO 99/24394 discloses that Chrysamine G and derivatives thereof bind to amyloid-β and thus may be suitable for diagnosis and therapy of Alzheimer's disease. The present inventors, however, have found that Chrysamine G is not effective in reducing amyloid-β aggregate formation in a cellular assay.

The present inventors now have identified compounds which bind to amyloid-β and are capable of reducing amyloid-β aggregate formation also in a cellular assay.

The present invention refers to a compound of formula I as defined herein or a physiologically acceptable salt, hydrate, solvate, tautomer, metabolite or prodrug thereof and the use of such a compound in medicine, particularly use in the treatment, diagnosis and or monitoring of a disease associated with, accompanied by and/or caused by protein misfolding or formation of protein aggregates, particularly amyloid misfolding or formation of amyloid aggregates.

Thus, a first aspect of the present invention refers to a compound of formula (I) or a physiologically acceptable salt, hydrate, solvate, tautomer, metabolite or prodrug thereof for use in medicine,

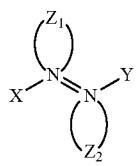

wherein
X is a 6- to 10-membered aromatic radical, wherein X comprises at least one first substituent different from H, and optionally at least one further substituent different from H, wherein the first substituent is selected from
—$NH_2$, —$NHR_1$, —$N(R_1)_2$,
—$N=NR_2$, —$NH-N=NR_2$, —$N=N-NHR_2$,
—OH, —$OR_3$, —$OCOR_3$,
—$NO_2$, —CN, —SCN, —NCS,
—COH, —$COR_4$
—$S(O)_nH$, —$S(O)_nR_5$, wherein n is 0, 1, 2 or 3, Y is a 5- or 6-membered aromatic or heteroaromatic radical, wherein Y optionally comprises at least one substituent different from H, $Z_1$ and $Z_2$ are free electron pairs or one of $Z_1$ and $Z_2$ is =O and the other a free electron pair, $R_1$ is in each case independently selected from $C_{1-8}$ alkyl, $C_{2-8}$ alkenyl, $C_{2-8}$ alkynyl or a 5- to 10-membered saturated or unsaturated cyclic radical, wherein $R_1$ optionally comprises at least one substituent different from H, or two $R_1$ form a 5- to 6-membered heterocyclic radical which optionally comprises at least one substituent different from H, $R_2$ is a 5- to 10-membered aromatic or heteroaromatic radical wherein $R_2$ optionally comprises at least one substituent different from H, $R_3$, $R_4$ and $R_5$
are in each case independently selected from $C_{1-8}$ alkyl or a 5- to 6-membered saturated or unsaturated cyclic radical, wherein each $R_3$, $R_4$ and $R_5$ optionally comprises at least one substituent different from H, with the proviso that when at least one of X and Y is substituted by at least one group selected from —COOH and —$SO_3$H, at least one of X and Y is substituted with at least one group —$NH_2$, —$NHR_1$ and —$N(R_1)_2$ as described above.

The present inventors have found that the compounds of formula (I) are capable of reducing amyloid-β monomer and/or dimer formation in vivo, i.e. in a cell-based assay. Thus, the compounds of the present invention preferably exhibit a reduction of amyloid-β monomer and/or dimer formation, e.g. in an assay as described in Example 3. In contrast thereto, Chrysamine G, the compound disclosed in WO99/24394, is ineffective in such an assay.

In the context of the present invention, the term "alkyl" refers to straight or branched chain hydrocarbon groups of 1 to 8 carbon atoms, preferably of 1 to 6 carbon atoms, more preferably 1-4 carbon atoms. Specific examples of alkyl groups are methyl, ethyl, propyl, i-propyl, n-butyl, sec-butyl or tert-butyl.

"Alkenyl" refers to a straight or branched hydrocarbon group containing at least one double bond, having from 2 to 8 carbon atoms, preferably 2 to 6 carbon atoms and more preferably 2 to 4 carbon atoms. Specific examples of alkenyl groups are ethenyl and propenyl.

"Alkynyl" refers to a straight or branched hydrocarbon group containing at least one triple bond, optionally further containing at least one double bond, having from 2 to 8 carbon atoms, preferably 2 to 6 carbon atoms. Specific examples are ethynyl and propynyl.

"Alkoxy" refers to an alkyl group as defined above linked to O. Specific examples are methoxy, ethoxy and propoxy.

The term "cyclic radical" refers to saturated or unsaturated hydrocarbon mono-, bi- or tricyclic ring systems optionally comprising heteroatoms such as N, O and/or S. Examples of saturated cyclic radicals are $C_{3-14}$ cycloalkyl, preferably $C_{3-8}$ cycloalkyl or $C_{5-14}$, preferably $C_{5-8}$ cyclo-heteroalkyl. Specific examples of saturated cyclic groups are cyclopropyl, cyclobutyl, cyclopentyl, cyclohexyl, pyrrolidinilyl, piperidinyl, piperazinyl, morpholinyl or tetrahydrofuranyl. Examples of unsaturated ring systems are non-aromatic unsaturated cyclic ring systems such as $C_{3-14}$, preferably $C_{3-8}$ cycloalkenyl, or $C_{5-14}$, preferably $C_{5-6}$ cycloheteroalkenyl. Specific examples are cyclopentenyl and cyclohexenyl. Further Examples are aromatic or heteroaromatic ring systems, e.g. $C_{6-14}$, preferably $C_{6-10}$ aromatic ring systems or heteroaromatic ring systems comprising at least one and up to five heteroatoms, such as N, O and/or S, e.g. $C_{5-14}$, preferably $C_{5-6}$ heteroaromatic ring systems. Specific examples of aromatic ring systems are phenyl, naphthyl and biphenyl. Specific examples of heteroaromatic groups are pyridinyl, pyrimidinyl, imidazolyl, pyrazolyl, triazolyl, pyrazinyl, tetrazolyl, furyl, thienyl, isoxazolyl, thiazolyl, oxazolyl, isothiazolyl, pyrrolyl, aminolinyl, isoquinolinyl, indolyl, benzimodazolyl, benzofuranyl, indazolyl, purinyl, benzothiazolyl, etc.

The term "halo" refers to fluorine, chlorine, bromine and iodine. Preferred are fluorine and chlorine.

The term "physiologically acceptable salt" refers to salts of the compounds of formula I with physiologically acceptable anions, e.g. inorganic anions such as chloride, sulfate, hydrogen sulfate etc. or organic anions, such as sulfonates, organic sulfates and carboxylates, or with physiologically acceptable cations, e.g. inorganic cations such as alkali-metal cations, e.g. lithium, sodium or potassium, alkaline earth metal cations, e.g. magnesium or calcium, or organic cations, e.g. amine or ammonium cations.

The terms "hydrate" and "solvate" relate to conjugates of the compound of formula (I) with water or other solvents.

The term "prodrug" refers to compounds that may be converted under physiological conditions to the compound of the invention. Thus, the term "prodrug" refers to a metabolic precurser of the compound of the invention.

The term "metabolite" refers to a compound which a compound of formula (I) is converted to under physiological conditions.

In formula (I), X is a 6- to 10-membered aromatic radical, particularly phenyl or naphthyl, and more particularly phenyl. X comprises at least one, e.g. one, two or three first substituents different from H and optionally at least one, e.g. one, two or three further substituents different from H.

In some embodiments, the at least one first substituent on X may be selected from $-NH_2$, $-NHR_1$, $-N(R_1)_2$, $-NO_2$, $-NCS$ and $-OH$, wherein $R_1$ is as defined above.

In some embodiments, X is selected from (i) phenyl comprising at least one first substituent on position 4, on positions 2 and 4 or on positions 2, 4 and 5, and particularly phenyl comprising a group $-NH_2$, $-NHR_1$ or $N(R_1)_2$ on position 4, or on positions 2 and 4, a group $-OH$ on position 4 or on positions 2 and 4, a group $-NO_2$ on position 2 or positions 2 and 4, or a group $-NCS$ on position 2, or (ii) naphth-1-yl comprising at least one first substituent on position 2, and particularly naphth-1-yl comprising a group $-NH_2$, $-NHR_1$ or $-N(R_1)_2$ on position 2 or a group $-OH$ on position 2.

Further substituents on X, if present, may e.g. be selected from $C_{1-8}$ alkyl, $C_{2-8}$ alkenyl, $C_{2-8}$ alkynyl, $C_{1-8}$ alkoxy, COOH, COO—$C_{1-8}$ alkyl, $CONH_2$, $CONH(C_{1-8}$ alkyl), $CO(C_{1-8}$ alkyl)$_2$, halo. The alkyl, alkenyl, alkynyl and alkoxy group may be further substituted e.g. by halo and/or OH.

$R_1$ is a group present on the first substituents $NHR_1$ and $N(R_1)_2$ on X. $R_1$ is particularly selected from $C_{1-4}$ alkyl, e.g. methyl and phenyl. $R_1$ may be unsubstituted or optionally may comprise at least one substituent different from H. If $R_1$ is alkyl, alkenyl, alkynyl, this substituent may be selected from halo and/or OH. If $R_1$ is a 5- to 10-membered saturated or unsaturated cyclic radical, e.g. phenyl, $R_1$ may be selected from $C_{1-4}$ alkyl (optionally halogenated), $C_{1-4}$ alkoxy (optionally halogenated), halo, $NO_2$ and/or OH. The same substituents may also be present on a 5-6 membered heterocyclic radical, which is formed from two $R_1$ groups.

Specific preferred groups $R_1$ are $NH_2$, $NH(CH_3)$, $N(CH_3)_2$, $NH(C_2H_5)$ or NH-phenyl.

A specific first substituent of X is NH-phenyl.

$R_2$ is present on the first substituents $-N=NR_2$, $-NH-N=NR_2$ and $-N=N-NHR_2$.

$R_2$ is particularly a 6- to 10-membered aromatic radical, e.g. phenyl or naphthyl. $R_2$ may be unsusbtituted or may comprise at least one substituent different from H. Examples of such substituents are as defined for $R_1$ (in the case that $R_1$ is a cyclic radical) and additionally $NO_2$, $NH_2$, $NH(C_{1-8}$ alkyl) (optionally halogenated) or $N(C_{1-8}$ alkyl)$_2$ (optionally halogenated).

$R_3$, $R_4$ and $R_5$ are preferably selected from $C_{1-6}$ alkyl, which may be unsusbtituted or optionally comprise at least one substituent different from H.

These substituents may be selected from the substituents present on $R_1$.

The group Y is a 5- to 6-membered aromatic or heteroaromatic radical which may be unsubstituted or optionally comprise at least one substituent different from H. Y may be phenyl or a heteroaromatic radical, particularly an N-heteroaromatic radical such as pyridyl, pyrrolyl, pyrazolyl or triazolyl, or an N-heteroaromatic radical comprising at least one S- or O-atom, such as thiazolyl or oxazolyl.

In some embodiments, Y is selected from phenyl, pyridyl such as pyrid-1-yl, pyrid-2-yl, pyrid-3-yl or pyrid-4-yl, thiazolyl, e.g. 1,3-thiazolyl, such as 1,3-thiazol-2-yl or triazolyl, e.g. 1,2,4-triazolyl such as 1,2,4-triazol-5-yl, and particularly Y is phenyl.

Y may be unsubstituted or comprise at least one substituent, e.g. selected from the first substituents present on X and the further substituents, optionally present on X. In some embodiments, Y is unsubstituted or comprises at least one substituent which is selected from $NH_2$, $NHR_1$, $N(R_1)_2$, OH and $NO_2$, wherein $R_1$ is as described above, $C_{1-6}$ alkyl or halo.

$Z_1$ and $Z_2$ may both be free electron pairs. Alternatively, $Z_1$ may be a free electron pair and $Z_2$ may be =O, or $Z_1$ may be =O and $Z_2$ may be a free electron pair.

In specific embodiments Y is phenyl, phenyl-p-$NO_2$, phenyl-m-N=N phenyl unsubstituted or substituted, phenyl-m-$NO_2$-p-OH, phenyl-p-$NH_2(N(CH_3)_2)$, phenyl-m-$SO_3H$, phenyl-m-$C_{1-6}$ alkyl (e.g. methyl) or phenyl-2,4-dihalo (e.g. dichloro).

In some embodiments the compound of formula (I) does not comprise a —COOH (or carboxylate) group. In some embodiments the compound of formula (I) does not comprise any acid-like functionality which contains an ionizable proton with a pKa of less than 6.

Specific examples or compounds of formula (I) are as follows:
N-phenyl-4-(phenyldiazenyl)aniline,
4-((4-nitrophenyl)diazenyl)-N-phenylaniline,
4-((4-nitrophenyl)diazenyl)aniline,
4-(phenyldiazenyl)phenol,
1-(phenyldiazenyl)naphthalen-2-ol,
1-(pyridin-2-yldiazenyl)naphthalen-2-ol,
4,4'-1,3-phenylenebis(diazene-2,1-diyl)dibenzene-1,3-diamine,
N-ethyl-1-((4-(-phenyldiazenyl)phenyl)diazenyl)naphthalen-2-amine,
4-((2,4-dinitrophenyl)diazenyl)-2-nitrophenol,
4-((4-aminophenyl)diazenyl)-N,N-dimethylaniline,
1,2-diphenyldiazene oxide,
1,2-diphenyldiazene,
4-((4-isothiocyanatophenyl)diazenyl)-N,N-dimethylaniline,
2-methyl-4-(o-tolyldiazenyl)aniline,
1-(4-ethoxy-3-methylphenyl)-2-p-tolyldiazene,
(3-((4-(phenylamino)phenyl)diazenyl)phenyl)sulfanolic acid,
4-(pyridin-2-yldiazenyl)benzene-1,3-diol, 4-((4-nitrophenyl)diazenyl)benzene-1,3-diol,
4-(thiazol-2-yldiazenyl)benzene-1,3-diol,
4-(phenyldiazenyl)benzene-1,3-diol,
4-((2,4-dihydroxyphenyl)diazenyl)benzenesulfonic acid,
4-((2,4-dihydroxyphenyl)diazenyl)-5-hydroxynaphthalene-2,7-disulfonic acid,
3-((2,4-dihydroxyphenyl)diazenyl)-4-hydroxybenzenesulfonic acid,
2,4-dihydroxy-5-(m-tolyldiazenyl)benzaldehyde,
4-((1H-1,2,4-triazol-5-yl)diazenyl)benzene-1,3-diol,
4-methyl-6-(thiazol-2-yldiazenyl)benzene-1,3-diol,
5-methoxy-2-(thiazol-2-yldiazenyl)phenol,
5-methyl-4-((4-nitrophenyl)diazenyl)benzene-1,3-diol,
4-((2,5-dichlorophenyl)diazenyl)benzene-1,3-diol,
1-((4-nitrophenyl)diazenyl)naphthalen-2-ol,
N,N-dimethyl-4-(phenyldiazenyl)aniline,
5-methyl-4-(thiazol-2-yldiazenyl)benzene-1,3-diol,
1-(4-nitrophenyl)-3-(4-(phenyldiazenyl)phenyl)triaz-1-ene,
or physiologically acceptable salts thereof.

The compounds of the present invention are suitable for therapeutic or diagnostic applications. Particularly for diagnostic applications, the compound of formula (I) may comprise at least one detectable group, e.g. a radioactive or non-radioactive detectable group. In one embodiment, the detectable group is a deuterium atom which is particularly a substituent of X or Y or a substituent of a group $NH_2$ or $NHR_1$, wherein at least one hydrogen atom is replaced by deuterium. Examples of radioactive substituents are or comprise isotopes of I, e.g. $^{123}$I, $^{125}$I or $^{131}$I, isotopes of Br, e.g. $^{75}$Br, $^{76}$Br or $^{77}$Br isotopes of F, e.g. $^{18}$F or $^{19}$F. In specific embodiments, the compound comprises at least one substituent which is an $^{18}$F or $^{19}$F atom or a group comprising an $^{18}$F or $^{19}$F atom, such as —$CH_2$—$^{18}$F, —$CH_2$—$^{19}$F, —$CH(^{18}F)_2$, —$CH(^{19}F)_2$, —$C^{18}F_3$, —$C(^{19}F)_3$, —$CH_2$—$CH_2$—$^{18}$F, $(^{19}F)$, O—$CH_2$—$^{18}$F, $(^{19}F)$ O—$CH_2$—$CH_2$—$^{18}$F, $(^{19}F)$, $CH_2$—$CH_2$—$CH_2$—$^{18}$F, $(^{19}F)$, O—$CH_2$—$CH_2$—$CH_2$—$^{18}$F, $(^{19}F)$ or aromatic compounds comprising at least one, e.g. 1-4 $^{18}$F or $^{19}$F groups. Such groups may be detected by suitable methods including MRS (Magnetic Resonance Spectroscopy), MRI (Magnetic Resonance Imaging), PET (Positron Emission Tomography), or SPECT (Single-Photon Emission Computed Tomography).

The compounds of formula (I) belong to the class of Azo-compounds. These compounds are well-known and commercially available, e.g. as described in the present Examples.

The present inventors have found that the compounds of formula (I) act as inhibitor of amyloid-β aggregate formation, and/or modulator of amyloid surface properties, and/or as activator of degradation or reduction of amyloid-β aggregates.

Thus, the compounds are suitable for medical applications, e.g. in human or veterinary medicine. Particularly the compounds may be used in the treatment, diagnosis and/or monitoring of a disease associated with, accompanied by and/or caused by protein misfolding, particularly amyloid-β misfolding or formation of protein aggregates, particularly of amyloid-(β aggregates.

The disease may e.g. be selected from Alzheimer's disease, Parkinson's disease, an amyloidosis such as αβ-amyloidosis, primary systemic amyloidosis, secondary systemic amyloidosis, senile systemic amyloidosis, familial amyloid polyneuropathy 1, hereditary cerebral amyloid angiopathy, hemodialysis-related amyloidosis, familial amyloid polyneuropathy III, Finnish hereditary systemic amyloidosis, type 2 diabetes, medullary carcinoma of thyroid, atrial amyloidosis, hereditary non-neuropathic systemic amyloidosis, injection-localized amyloidosis, hereditary renal amyloidosis, amyotrophic lateral sclerosis, schizophrenia, sickle cell anaemia, unstable haemoglobin inclusion body haemolysis, α1-antitrypsin deficiency, antithrombin deficiency, thromboembolic disease, spinobulbar muscular atrophy (Kennedy disease), dentatorubral-pallidoluysian atrophy (Haw River syndrome), Huntington's disease, spinocerebellar ataxia type 1, spinocerebellar ataxia type 2, spinocerebellar ataxia type 3 (Machado-Joseph disease), spinocerebellar ataxia type 6, spinocerebellar ataxia type 7, spinocerebellar ataxia type 17, transmissible spongiform encephalopathies (prion diseases): Bovine spongiform encephalopathy, kuru, Gerstmann-Straeussler-Scheinker syndrome, fatal familial insomnia, scrapie, Creutzfeldt-Jakob disease and variant Creutzfeldt-Jakob disease. Particularly, the disease is an amyloidosis, in particular (β-amyloidosis.

The invention, however, also refers to a non-medical use of a compound of formula (I) as an inhibitor of protein misfolding and/or the accumulation of a misfolded protein or protein aggregate, and/or as a modulator of amyloid surface properties, and/or as an activator of degradation of a misfolded protein or a protein aggregate. The protein is particularly selected from amyloid-proteins. More particularly, the protein is amyloid-β.

A further aspect of the present invention refers to a pharmaceutical and/or diagnostic composition comprising at least one compound of formula (I) and optionally a physiologically acceptable carrier, e.g. a carrier suitable for therapeutic or diagnostic applications. The composition may be in form of a solution, suspension, emulsion or solid substance, e.g. a tablet or capsule. Preferably, the composition is a dosage form suitable for oral administration.

Optionally, the composition may contain other active agents, e.g. therapeutic agents for the treatment of amyloid-associated diseases as indicated above. The composition of the present invention comprises at least one compound of formula (I) in a pharmaceutically or diagnostically effective amount. This amount may vary broadly according to the desired application from e.g. 0.01 mg to 1000 mg or even higher. The composition may be administered to a subject in need thereof, e.g. a human patient, by any suitable route, e.g. orally, topically, transdermally, rectally or parenterally, e.g. by intravenous, intraarterial, intramuscular, subcutaneous, intrathecal or intraperitoneal injection or infusion. Preferably, the composition is administered orally.

For diagnostic applications, it may be preferred to use a compound comprising at least one detectable group and to detect binding of the compound to amyloid species in vivo, e.g. as described above by MRI, PET or SPECT.

Further, the invention shall be explained in more detail by the following figures and examples.

FIG. 1:
Structure of compounds 1-31 according to the invention, comparative compounds 32-34 (ineffective compounds) and comparative compounds A-C (according to WO99/24394).

Figure 2:
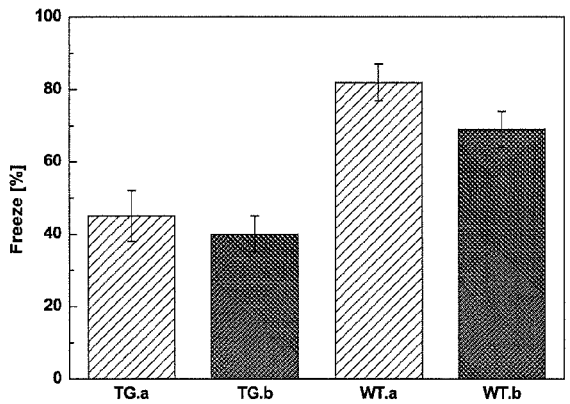
Figure 2:
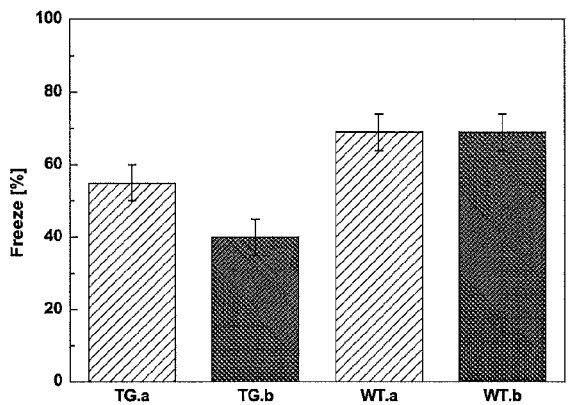
Figure 2:
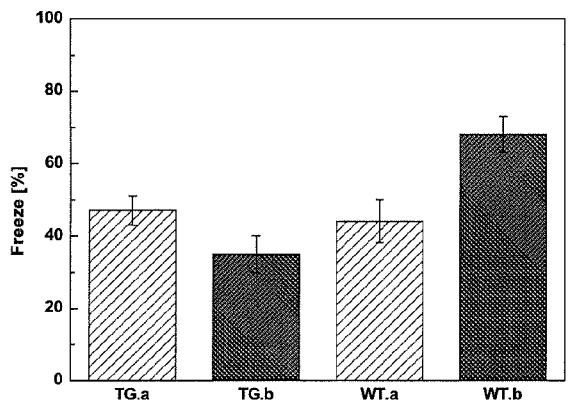

FIG. 2:
Effect of administration of compounds 1(A), 2(B) and 9(C) on the contextual memory of Tg2576 mice.
Notes:
"TG.a" transgenic group, treated
"WT.a" wild type group, treated
"TG.b" transgenic group, untreated
"WT.b" wild type group, untreated FIG. 3:
Effect of administration of compound 2 on nest building behaviour in 5XFAD mice. "Control": untreated animals; "low concentration": animals treated with a lower concentration (62.5 mg/kg feed) of compound 2; "high concentration":

animals treated with a higher concentration (625 mg/kg feed) of compound 2. 3a: Nestlet usage; 3b: Nestlet quality score.

EXAMPLES

Example 1

Compounds 1-23 and 25-36 were obtained from commercial manufacturers as indicated. Compound 24 was prepared as indicated.

| Compound | Name |
|---|---|
| Compound 1 | N-phenyl-4-(phenyldiazenyl)aniline |
| | Acros Organics, Geel, Belgium |
| Compound 2 | 4-((4-nitrophenyl)diazenyl)-N-phenylaniline |
| | Acros Organics, Geel, Belgium |
| Compound 3 | 4-((4-nitrophenyl)diazenyl)aniline |
| | Acros Organics, Geel, Belgium |
| Compound 4 | 4-(phenyldiazenyl)phenol |
| | Acros Organics, Geel, Belgium |
| Compound 5 | 1-(pyridin-2-yldiazenyl)naphthalen-2-ol |
| | Alfa Aesar, Karlsruhe, Germany |
| Compound 6 | 4,4'-1,3-phenylenebis(diazene-2,1-diyl)dibenzene-1,3-diamine |
| | Alfa Aesar, Karlsruhe, Germany |
| Compound 7 | N-ethyl-1-((4-(-phenyldiazenyl)phenyl)diazenyl)-naphthalen-2-amine |
| | Acros Organics, Geel, Belgium |
| Compound 8 | 4-((2,4-dinitrophenyl)diazenyl)-2-nitrophenol |
| | Sigma-Aldrich, Steinheim, Germany |
| Compound 9 | 4-((4-aminophenyl)diazenyl)-N,N-dimethylaniline |
| | Acros Organics, Geel, Belgium |
| Compound 10 | 4-((4-isothiocyanatophenyl)diazenyl)-N,N-dimethylaniline |
| | Acros Organics, Geel, Belgium |
| Compound 11 | sodium (3-((4-phenylamino)phenyl)diazenyl)phenyl)-sulfanolate |
| | Acros Organics, Geel, Belgium |
| Compound 12 | 4-(pyridin-2-yldiazenyl)benzene-1,3-diol |
| | Sigma-Aldrich, Steinheim, Germany |
| Compound 13 | 4-((4-nitrophenyl)diazenyl)benzene-1,3-diol |
| | Acros Organics, Geel, Belgium |
| Compound 14 | 4-(thiazol-2-yldiazenyl)benzene-1,3-diol |
| | Sigma-Aldrich, Steinheim, Germany |
| Compound 15 | 4-(phenyldiazenyl)benzene-1,3-diol |
| | Sigma-Aldrich, Steinheim, Germany |
| Compound 16 | 2,4-dihydroxy-5-(m-tolyldiazenyl)benzaldehyde |
| | Sigma-Aldrich, Steinheim, Germany |
| Compound 17 | 4-((1H-1,2,4-triazol-5-yl)diazenyl)benzene-1,3-diol |
| | Sigma-Aldric'h, Steinheim, Germany |
| Compound 18 | 4-methyl-6-(thiazol-2-yldiazenyl)benzene-1,3-diol |
| | Sigma-Aldrich, Steinheim, Germany |
| Compound 19 | 5-methyl-4-((4-nitrophenyl)diazenyl)benzene-1,3-diol |
| | Sigma-Aldrich, Steinheim, Germany |
| Compound 20 | 4-((2,5-dichlorophenyl)diazenyl)benzene-1,3-diol |
| | Sigma-Aldrich, Steinheim, Germany |
| Compound 21 | N,N-dimethyl-4-(phenyldiazenyl)aniline |
| | Sigma-Aldrich, Steinheim, Germany |
| Compound 22 | 5-methyl-4-(thiazol-2-yldiazenyl)benzene-1,3-diol |
| | Sigma-Aldrich, Steinheim, Germany |
| Compound 23 | 1-(4-nitrophenyl)-3-(4-(phenyldiazenyl)phenyl)-triaz-1-ene |
| | Sigma-Aldrich, Steinheim, Germany |
| Compound 24 | 4-((4-aminophenyl)diazenyl)-N-phenylaniline |
| | 4-((4-nitrophenyl)diazenyl)-N-phenylaniline (300 mg, 0.94 mmol, Sigma-Aldrich) was stirred under argon atmosphere with sodium borohydride (53 mg, 1.40 mmol, Sigma-Aldrich) and palladium acetate (10 mg, 0.04 mmol, Sigma-Aldrich) in ethanol (25 mL, Roth) for 18 h at room temperature. The reaction was quenched with water (30 mL) and the crude product extracted two times with dichloromethane (2 × 20 mL, Acros Organics). The organic layers were combined, dried over sodium sulfate and evaporated. The product was purified by column chromatography (Silica gel 60, <0.063 mm, Merck, 95:5 $CCl_2H_2$ : $CH_3OH$) to yield the compound as dark/brown solid (46 mg, 16.9%). |
| Compound 25 | 1-(phenyldiazenyl)naphthalen-2-ol |
| | Acros Organics, Geel, Belgium |
| Compound 26 | 2-methyl-4-(o-tolyldiazenyl)aniline |
| | Sigma-Aldrich, Steinheim, Germany |
| Compound 27 | sodium 4-((2,4-dihydroxyphenyl)diazenyl)-benzenesulfonate |
| | Sigma-Aldrich, Steinheim, Germany |
| Compound 28 | 4-((2,4-dihydroxyphenyl)diazenyl)-5-hydroxynaphthalene-2,7-disulfonic acid |
| | Sigma-Aldrich, Steinheim, Germany |
| Compound 29 | sodium 3-((2,4-dihydroxyphenyl)diazenyl)-4-hydroxybenzenesulfonate |
| | Sigma-Aldrich, Steinheim, Germany |
| Compound 30 | 5-methoxy-2-(thiazol-2-yldiazenyl)phenol |
| | Acros Organics, Geel, Belgium |
| Compound 31 | 1-((4-nitrophenyl)diazenyl)naphthalen-2-ol |
| | Alfa Aesar, Karlsruhe, Germany |
| Comparative Compound 32 | 1,2-diphenyldiazene oxide |
| | Sigma-Aldrich, Steinheim, Germany |
| Comparative Compound 33 | 1,2-diphenyldiazene |
| | Sigma-Aldrich, Steinheim, Germany |
| Comparative Compound 34 | 1-(4-ethoxy-3-methylphenyl)-2-p-tolyldiazene |
| | Sigma-Aldrich, Steinheim, Germany |
| Comparative Compound A | 2-hydroxy-5-(phenyldiazenyl)benzoic acid/ Half Chrysamine G |
| | Sigma-Aldrich, Steinheim, Germany |
| Comparative Compound B | 2-((4-hydroxyphenyl)diazenyl)Benzoic acid |
| | Merck, Darmstadt, Germany |
| Comparative Compound C | (5-5'-biphenyl-4,4'-diylbis(diazene-2,1-diyl)bis-(2-hydroxybenzoic acid))/Chrysamine G |
| | Sigma-Aldrich, Steinheim, Germany |
| | The sodium salt was converted to the free acid. |
| | The conversion was monitored by TLC and $^1$H-NMR. |
| | $^1$H-NMR (Bruker Avance 300 MHz spectrometer; chemical shifts are reported in parts per million downfield from the internal standard tetramethylsilane, 0.0 ppm; $d_6$-DMSO) ppm: 7.43 (s, 1H, NH), 7.10 (d, 2H, J = 7.2 Hz, Ar—H), 7.07 (d, 2H, J = 7.5 Hz Ar—H), 6.82 (d, 2H, J = 8.6 Hz, Ar—H), 6.76 (d, 2H, J = 7.8 Hz, Ar—H), 6.62-6.57 (m, 3H, Ar—H), 6.54 (d, 2H, J = 8.6 Hz, Ar—H), 4.74 (s, 2H, $NH_2$). |

Example 2

Thioflavin T-Assay

The Thioflavin T (Thio T)-assay measures the beta-sheet content of an amyloid-beta preparation. Thioflavin T is a fluorescent substance, which binds specifically to (β-sheet structures, such as those in amyloid fibrils. The binding results in a shift of the Thio T fluorescence spectrum and an enhancement of the fluorescence signal (LeVine, H., Methods in Enzymology 1999). The Thio T-assay can be used to assess the inhibitory effect of compounds on the cascade of Aβ aggregation.

The assay was carried out as follows:

Preparation of the $Aβ_{1-42}$ peptide stock solution: $Aβ_{1-42}$ peptide (3 mg) was dissolved with 3 ml HFIP (1,1,1,3,3,3-hexafluoro-2-propanol) and the solvent was removed under a nitrogen stream. The peptide was re-dissolved in DMSO (1 mM), aliquoted and stored at −80° C. The solution was centrifugated (55000 rpm, 20° C.) and the supernatant was used for the assay.

Sampling: The compounds were dissolved with DMSO and diluted with NaP-buffer (100 mM NaCl, 10 mM $NaH_2PO_4$, pH=7.4). Various concentrations of each compound were mixed with a 30 μM $Aβ_{1-42}$ peptide. The reaction mixtures were incubated in 96 well PCR plates from Costar (#6551). The plates were covered with plate sealers from Bio-Stat (#896125) and stored for 48 h in a moisture chamber at 37° C. After the incubation time, an aqueous Thio T (20 mM) stock solution was diluted with NaP-buffer to a final concentration of 100 μM and mixed with aliquots from the compound samples in black 96 well plates with transparent bottom (Corning, #3651). Fluorescence was determined at an excitation wavelength of 420 nm and an emission wavelength of 490 nM. All concentrations were evaluated in triplicate. The $IC_{50}$ values were obtained from measurements of fluorescence of compound treated samples against DMSO treated control samples.

The results are shown in Table 1.

TABLE 1

| Compound | ThioT: $IC_{50}$ [μM] |
|---|---|
| 1 | 4.5 |
| 2 | 1.7 |
| 3 | 3.3 |
| 4 | 13.2 |
| 5 | 12.2 |
| 6 | 0.9 |
| 7 | 3.1 |
| 8 | 2.6 |
| 9 | 2.1 |
| 10 | 0.4 |
| 11 | 9.5 |
| 12 | 3.0 |
| 13 | 1.1 |
| 14 | 4.8 |
| 15 | 2.2 |
| 16 | 3.3 |
| 17 | 8.0 |
| 18 | 2.4 |
| 19 | 0.9 |
| 20 | 1.3 |
| 21 | 16.8 |
| 22 | 2.4 |
| 23 | 1.1 |
| 24 | 4.8 |
| 25 | 43.9 |
| 26 | 31.8 |
| 27 | 61.5 |
| 28 | 19.2 |
| 29 | 19.8 |
| 30 | 27.4 |
| 31 | 87.1 |
| Comparative Compound | |
| 32 | — |
| 33 | 1087.2 |
| 34 | 105.3 |
| A | 57.4 |
| B | 736.1 |
| C | 0.5 |

Notes:
"—" no effect

Example 3

Cell-Based Aβ-Monomer and Dimer Assay

The cell-based Aβ-assay measures the amount of low molecular weight Aβ-species in the culture medium of mutant amyloid precursor protein (APP)-expressing cells. It is used to test the effect of chemical compounds on the formation of Aβ-monomers and dimers. After incubating cells with potentially effective compounds, the Aβ-monomers and dimers can be immunoprecipitated from cell culture media and detected by immunoblotting. In this way, chemical compounds that modulate Aβ-monomer production and dimer formation can be identified.

The assay was carried out as follows:

Chinese hamster ovary (CHO) cells stably expressing the V717F Alzheimer's disease mutation in the amyloid precursor protein (APP) isoform APP751 (also called 7PA2 cells) (Walsh D. M. et al, Nature 2002) were incubated for 16-20 hours with compounds diluted to a final concentration of 20 μM in D-MEM containing 4.5 g/l glucose and L-glutamine. The conditioned media containing secreted Aβ monomers and dimers were collected, cleared from remaining cells by centrifugation at 500×g and subjected to immunoprecipitations using Aβ specific antibodies and protein G sepharose beads in a final concentration of 50 mM Tris-HCl pH 7.5. Samples were incubated over night at 4° C. and beads were pelleted by centrifugation. The supernatant was removed and beads were washed once with STEN buffer (50 mM Tris-HCl pH 7.5, 150 mM NaCl, 2 mM EDTA, 0.2% BSA, 1% NP-40), once with SDS-STEN buffer (STEN buffer+0.1% SDS) and again with STEN buffer. Beads were eluted with 2× NuPAGE LDS sample buffer (Invitrogen) at 95° C. for 10 min and samples were loaded onto NuPAGE 4-12% Bis-Tris gels (Invitrogen). The effect of compounds on the amount of secreted Aβ monomers and dimers was evaluated by immunoblotting using the anti-Aβ antibody 6E10, peroxidase-coupled secondary antibodies and a chemiluminescent substrate. As control, the effect of compound solvent (DMSO) on Aβ monomer and dimer formation was analyzed. Further, immunoprecipitations with control antibodies as well as immunoprecipitations from CHO cells not expressing mutant APP were performed.

The results are shown in Table 2.

TABLE 2

| Compound | Dimer reduction |
|---|---|
| 1 | ++ |
| 2 | ++ |
| 3 | − |
| 4 | − |
| 5 | toxic |
| 6 | toxic |
| 7 | − |
| 8 | toxic |
| 9 | + |
| 10 | ++ |
| 11 | − |
| 12 | − |
| 13 | − |
| 14 | n.d. |
| 15 | − |
| 16 | n.d. |
| 17 | n.d. |
| 18 | n.d. |
| 19 | n.d. |
| 20 | ++ |
| 21 | ++ |
| 22 | − |
| 23 | − |
| 24 | ++ |
| 25 | − |
| 26 | toxic |
| 27 | − |
| 28 | − |
| 29 | n.d. |
| 30 | − |
| 31 | n.d. |
| Competitive Example | |
| 32 | − |
| 33 | − |

TABLE 2-continued

| | |
|---|---|
| 34 | toxic |
| A | - |
| B | - |
| C | - |

| Compound | Monomer reduction |
|---|---|
| 12 | ++ |
| 13 | ++ |

Notes:
"−" no effect
"+" strong effect
"++" very strong effect
"toxic": compounds exhibit cellular toxicity Example 4

Cytotoxicity on HepG2 Cells

The Alamar Blue assay measures the mitochondrial activity, which is reduced when toxic compounds are added to cells. The $IC_{50}$ value indicates the concentration of a certain compound which reduces cell viability by 50%.

Cell viability was assayed on HepG2 cells. HepG2 cells were cultured in 96-well black culture plates with transparent bottom in RPMI medium (1% L-Glu, 10% FCS). 3 hours after plating, different drug concentrations (0.1 μM-100 μM) or DMSO as control were added. Chlorpromazine hydrochloride (Sigma, # C0982) and cycloheximide (Sigma, # C1988) were used as control substances. Each concentration was run in triplicate. After 48 hours of incubation, Alamar Blue reagent (BIOSOURCE, # DAL1100) was added and plates were incubated for 4 hours at 37° C. Absorbance was measured in a micro-plate reader (Tecan, Infinite M200) at 570 nm and 600 nm. The results are shown in Table 3.

TABLE 3

| Example | Cytotoxicity HepG2 $IC_{50}$ [μM] |
|---|---|
| 1 | not toxic up to 30 μM |
| 2 | not toxic up to 100 μM |
| 3 | not toxic up to 100 μM |
| 4 | ~90 |
| 5 | not toxic up to 10 μM |
| 6 | ~11 |
| 7 | not toxic up to 3 μM |
| 8 | not toxic up to 3 μM |
| 9 | not toxic up to 100 μM |
| 10 | not toxic up to 100 μM |
| 11 | not toxic up to 100 μM |
| 12 | not toxic up to 1 μM |
| 13 | ~2 |
| 14 | not toxic up to 3 μM |
| 15 | ~31 |
| 16 | not toxic up to 30 μM |
| 17 | not toxic up to 100 μM |
| 18 | ~13 |
| 19 | ~41 |
| 20 | ~3 |
| 21 | not toxic up to 100 μM |
| 22 | ~101 |
| 23 | not toxic up to 30 μM |
| 24 | not toxic up to 30 μM |
| Chlorpromazine | 14.1 |

Example 5

Detection of Compounds After In Vivo Administration

For the i.v. application 5 mg test compound/kg body weight was administrated once in the caudal varix of a B6C3 mouse (The Jackson Laboratories). For this kind of application and oral gavage administration a formulation with 10% ethanol, 15% Solutol HS 15(BASF) and 75% water was produced. The total volume for oral gavage administration was adapted to the mouse weight.

For oral administration the drug concentrations were calculated from the IC50 value of the ThioT assay. For oral gavage administration three different concentrations were analyzed. 30 min. after the last application of five or seven single doses over two or three consecutive days, sampling took place. Brain samples from the i.v. and oral gavage administration were evaluated. For preparation of feeding pellets, a single concentration was determined.

Brain samples were taken after one week feeding. All positively tested compounds were detectable at the lowest respective concentration mentioned below. The feeding pellets were prepared by ssniff Spezialdiäten GmbH, Soest, Germany with animal feed PS M-Z, 10 mm.

Employed concentrations for oral administration:

Compound 1: oral gavage administration: 219.72 mg/kg body weight, 109.86 mg/kg body weight, 21.97 mg/kg body weight (3 days, 7 appl.); feeding pellet preparation: 71.89 mg/kg body weight and day*.

Compound 2: oral gavage administration: 167.54 mg/kg body weight, 83.77 mg/kg body weight, 16.75 mg/kg body weight (3 days, 6 appl.); feeding pellet preparation: 418.85 mg/kg body weight and day*.

Compound 8: oral gavage administration: 210.98 mg/kg body weight, 105.49 mg/kg body weight and day*.

Compound 9: oral gavage administration: 138.60 mg/kg body weight, 69.30 mg/kg body weight, 13.86 mg/kg body weight (2 days, 5 appl.); feeding pellet preparation: 34.65 mg/kg body weight and day*.

Compound 10: oral gavage administration: 79.20 mg/kg body weight, 39.60 mg/kg body weight, 7.92 mg/kg body weight (2 days, 5 appl.); feeding pellet preparation: 198.00 mg/kg body weight and day*.

Compound 13: oral gavage administration: 112.90 mg/kg body weight, 56.45 mg/kg body weight, 11.29 mg/kg body weight (3 days, 6 appl.); feeding pellet preparation: 282.25 mg/kg body weight and day*.

Compound 18: oral gavage administration: 178.70 mg/kg body weight, 89.85 mg/kg body weight (2 days, 5 appl.).

(* theoretical max. possible daily drug uptake)

The results are shown in Table 4.

TABLE 4

| Compound | i.v. administration | oral administration |
|---|---|---|
| 1 | ++ | ++[a), b)] |
| 2 | ++ | ++[a), b)] |
| 5 | ++ | n.d. |
| 6 | ++ | n.d. |
| 7 | ++ | n.d. |
| 8 | ++ | ++[a)]/n.d.[b)] |
| 9 | ++ | ++[a)]/+[b)] |
| 10 | ++ | ++[a), b)] |
| 12 | − | n.d. |
| 13 | ++ | ++[a), b)] |
| 14 | − | n.d. |
| 18 | ++ | ++[b)]/n.d.[b)] |
| 19 | ++ | n.d. |
| 20 | ++ | n.d. |
| 22 | − | n.d. |

Notes:
n.d. not determined
[a)] oral gavage administration
[b)] feeding pellet preparation
"+" weak detectable
"++" strong detectable
"−" not detectable.

Compounds were given to mice intravenously or orally (by oral gavage administration or in the feeding pellets).

All examined compounds showed good detectability in the brain after i.v. administration, with the exception of compounds 12, 14 and 22. The detectability after oral administration was excellent for compounds 1, 2, 8, 9, 10, 13 and 18. The results indicate very good blood-brain permeability for the whole compound family and a more than sufficient resorption (Table 4).

Example 6

Effect of Compounds In Vivo

Groups of Tg2576 mice overexpressing the 695-amino acid isoform of human amyloid precursor protein containing a Lys670→Asn, Met671→Leu mutation (Hsiao, K. Science 1996) and wildtype control mice (13-21 per phenotype) were conditioned on day 1 by placing a subject mouse in a contextual fear conditioning chamber (Med Associates, Georgia, Vt.). Exploration was allowed for 2 min, and an auditory cue was presented for 15 s accompanied by an electrical foot shock during the last 2 s. This procedure was repeated and mice were removed from the chamber after 30 s. Twenty hours later, mice were returned to the chamber in which conditioning occured, and their freezing behaviour (fear) was monitored. Freezing was defined as the lack of all movements, except those required for breathing (Comery, T. A., et al. Journal of Neuroscience, 2005). Data were analysed by two-way ANOVA in the S programming environment, followed by Fischer's least significant difference (LSD) pairwise comparison of group means at the $p<0.05$ significance level.

The contextual fear conditioning paradigm is a form of Pavlovian learning in which an association is made between stimuli and their aversive consequences. Studies of brain function implicate the amygdala in regulating fear, and the hippocampus in regulating the learning of the context in which a fearful event occurred.

The brain circuitry in wild type mice is intact and they are better able to associate an aversive foot shock with the context or environment in which the shock took place. They therefore show more freezing. Transgenic Alzheimer mice have compromised brain circuitry due to the toxic effects of amyloid-beta protein. They are therefore less able to associate an aversive shock with a context and show less freezing.

A substance that reverses the toxic effects of amyloid-beta in Alzheimer's mice will help in reconsolidating the impaired brain circuitry so that these mice begin to show more fear (freezing behavior) after treatment. This paradigm is therefore a robust method for showing the effect of drug candidate molecules in Alzheimer mice.

This paradigm is of clinical relevance to humans because degeneration of the amygdala and hippocampus play a role in the impairment of learning and memory of individuals affected by Alzheimer's disease.

Long-term administration of Compounds 1, 2 and 9 via feeding pellets for 12 weeks resulted in an improvement in contextual memory of 9-month-old Tg2576 mice. The results are shown in FIG. 2A)-C).

Example 7

Effect of Compounds In Vivo

Groups (15-18 per genotype) of 6-week-old 5XFAD mice (plaque deposition begins at 8 weeks) were treated for 8.5 months with compound 2. One hour before the dark phase, mice were housed individually in a cage with wood-chip bedding material. Each mouse was given 3 g of nestlet material made of compressed cotton (Lillico Biotech, UK). The amount of intact, i.e. non-used, nesting material was weighed after 16 hours and nest building was assessed using the following rating scale (Deacon et al., 2006, Tomida et al., 2009): 1, >90% intact; 2, 50-90% intact; 3, 10-50% intact: 4, 0-10% intact, but flat nest; 5, 0-10%, with nests higher than the mice. The amount of intact nesting material was weighed. The data were non-normally distributed.

Non normally distributed data were analyzed by a Kruskal Wallis test. A post-hoc test using Mann-Whitney tests with Bonferroni corrections was then used for group comparisons.

Nest building is one of several species-typical behavior in mice seen in semi-naturalistic situations. It has been shown to be sensitive to damages of some brain regions, like the hippocampus and the frontal cortex. Alzheimer's disease in 5XFAD mice will damage these areas, leading to memory impairments in some standard cognitive tests, and to an impairment of species-typical behaviors like nesting.

The brain circuitry of wild type mice is intact so they show robust nest building behavior. Transgenic 5XFAD on the other hand have impaired brain circuitry due to the noxious effects of human amyloid-beta protein. They are therefore less able to fulfill this important house-keeping species typical behavior (Deacon R M. (2006): Assessing nest building in mice. Nat Protoc. 2006; 1(3):1117-9; Tomida et al (2009): Usp46 is a quantitative trait gene regulating mouse immobile behavior in the tail suspension and forced swimming tests. Nat Genet. 2009 June; 41(6):688-95. Epub 2009 May 24.).

Based on our previous results with Tg2576, we hypothesized that compound 2 will equally reverse the toxic effects of amyloid-beta in 5XFAD Alzheimer's mice and rescue this important function so that these mice should improve their nest building ability. This paradigm is a robust method for rapid tests showing the consolidation of nest building function in 5XFAD mice.

This paradigm is of clinical relevance to humans because Alzheimer's disease progression leads to loss of relational housekeeping ability in patients due to destruction of areas of the brain like the hippocampus and cortex.

Long term administration of compound 2 as pelleted mouse chow for 8.5 months led to improved nest building behavior in 5XFAD mice. A rescue of this impairment in treated transgenic mice is an indirect proof that the compounds according to the invention reverse the damages caused by Alzheimer's Disease in the hippocampus, an organ responsible for memory, and the cortex.

Figure 3A:
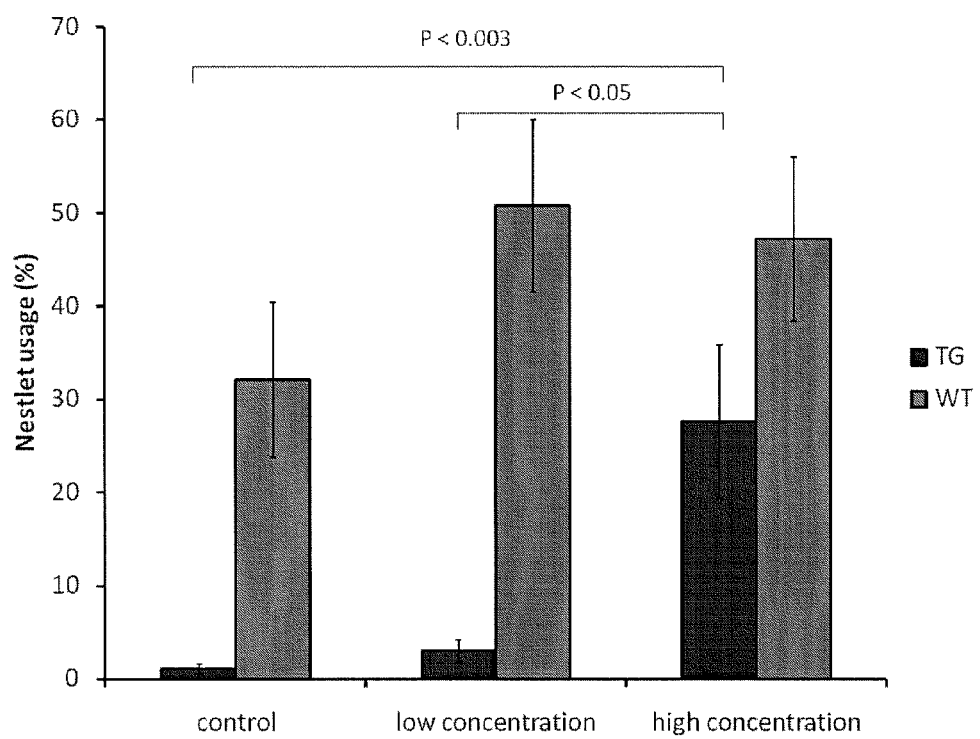

As shown in FIG. 3a, treated and untreated wild-type mice show robust nest building behavior, whereas the transgenic 5XFAD mice do not exhibit such distinct nest building behavior. However, the nest building behavior of both, transgenic and wild-type mice is increased as compared to the control mice when administering compound 2. From FIG. 3, it arises that the nest building behavior in transgenic mice could be significantly enhanced as compared to the control mice by the treatment of the subject with higher concentrations of compound 2.

Figure 3B:
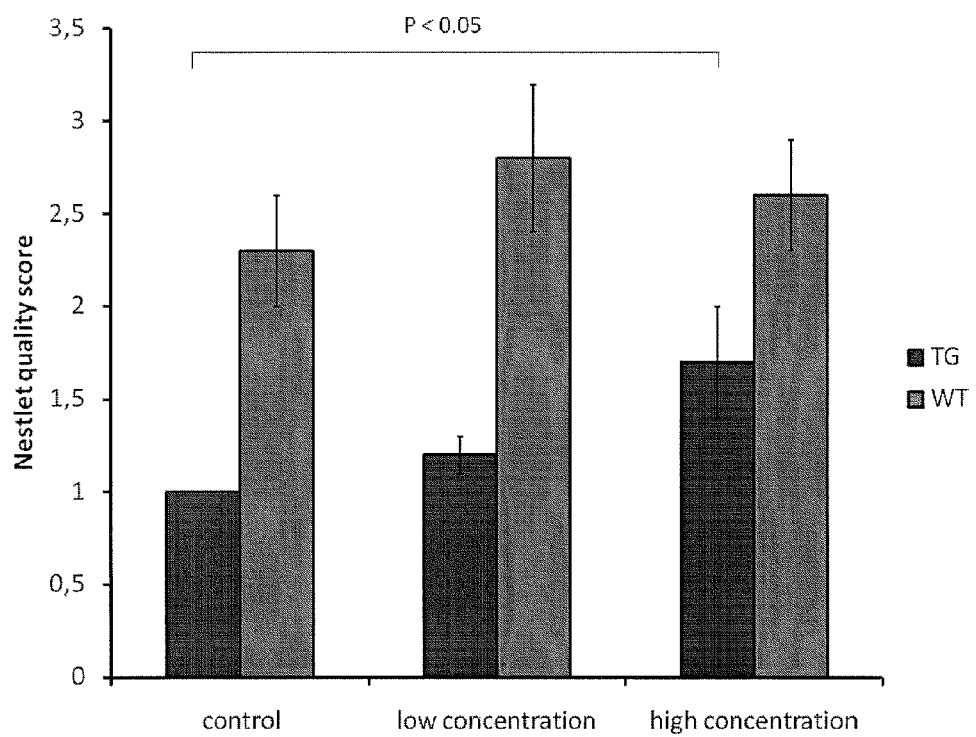

As shown in FIG. 3b, the transgenic 5XFAD mice have a reduced nestlet quality score, which means that a minor amount of nesting material is used for building nestlets, as compared to the wild-type mice. The nestlet quality score, however, increases for both, transgenic and wild-type mice, as compared to the control mice, when administering compound 2. The results in FIG. 3b clearly correlate to the findings in FIG. 3a.

The Following Items are Part of the Description:

1. A compound of formula I

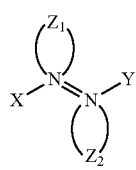

(I)

or a physiologically acceptable salt, hydrate, solvate, tautomer, metabolite or prodrug thereof for use in medicine, wherein X is a 6- to 10-membered aromatic radical, wherein X comprises at least one first substituent different from H, and optionally at least one further substituent different from H, wherein the first substituent is selected from
—$NH_2$, —$NHR_1$, —$N(R_1)_2$,
—$N=NR_2$, —NH—$N=NR_2$, —N=N—$NHR_2$,
—OH, —$OR_3$, —$OCOR_3$,
—$NO_2$, —CN, —SCN, —NCS,
—COH, —$COR_4$
—$S(O)_nH$, —$S(O)_nR_5$, wherein n is 0, 1, 2 or 3, Y is a 5- or 6-membered aromatic or heteroaromatic radical, wherein Y optionally comprises at least one substituent different from H, $Z_1$ and $Z_2$ are free electron pairs or one of $Z_1$ and $Z_2$ is =O and the other a free electron pair, $R_1$ is in each case independently selected from $C_{1-8}$ alkyl, $C_{2-8}$ alkenyl, $C_{2-8}$ alkynyl or a 5- to 10-membered saturated or unsaturated cyclic radical, wherein $R_1$ optionally comprises at least one substituent different from H, or two $R_1$ form a 5- to 6-membered heterocyclic radical which optionally comprises at least one substituent different from H, $R_2$ is a 5- to 10-membered aromatic or heteroaromatic radical wherein $R_2$ optionally comprises at least one substituent different from H, $R_3$, $R_4$ and $R_5$
are in each case independently selected from $C_{1-8}$ alkyl or a 5- to 6-membered saturated or unsaturated cyclic radical, wherein each $R_3$, $R_4$ and $R_5$ optionally comprises at least one substituent different from H, with the proviso that when at least one of X and Y is substituted by at least one group selected from —COOH and —$SO_3H$, at least one of X and Y is substituted with at least one group —$NH_2$, —$NHR_1$ and —$N(R_1)_2$ as described above.

2. The compound of item 1, which does not comprise a —COOH group.

3. The compound of item 1 or 2, wherein the at least one first substituent on X is selected from
—$NH_2$, —$NHR_1$, —$N(R_1)_2$,
—$NO_2$, —NCS,
—OH,
wherein $R_1$ is as defined in item 1.

4. The compound of any one of items 1-3, wherein X is phenyl or naphthyl, and particularly X is phenyl, and wherein X is particularly
(i) phenyl comprising at least one first substituent on position 4, on positions 2 and 4 or on positions 2, 4 and 5, and particularly X is phenyl comprising a group —$NH_2$, —$NHR_1$ or $N(R_1)_2$ on position 4, or on positions 2 and 4, a group —OH on position 4 or on positions 2 and 4, a group —$NO_2$ on position 2 or positions 2 and 4, or a group —NCS on position 2, or
(ii) naphth-1-yl comprising at least one first substituent on position 2, and particularly X is naphth-1-yl comprising a group —$NH_2$, —$NHR_1$ or —$N(R_1)_2$ on position 2 or a group —OH on position 2.

5. The compound of any one of items 1-4, wherein Y is phenyl, pyridyl such as pyrid-1-yl, pyrid-2-yl, pyrid-3-yl or pyrid-4-yl, thiazolyl, e.g. 1,3-thiazolyl, such as 1,3-thiazol-2-yl or triazolyl, e.g. 1,2,4-triazolyl such as 1,2,4-triazol-5-yl, and particularly Y is phenyl, and wherein Y is particularly unsubstituted or comprises at least one substituent which is selected from $NH_2$, $NHR_1$, $N(R_1)_2$, OH and $NO_2$, wherein $R_1$ is as described above, $C_{1-6}$ alkyl or halo.

6. The compound of any one of items 1-5, wherein $R_1$ is selected from $C_{1-4}$ alkyl, e.g. methyl and phenyl.

7. The compound according to any one of items 1-6, which is selected from
N-phenyl-4-(phenyldiazenyl)aniline,
4-((4-nitrophenyl)diazenyl)-N-phenylaniline,
4-((4-nitrophenyl)diazenyl)aniline,
4-(phenyldiazenyl)phenol,
1-(phenyldiazenyl)naphthalen-2-ol,
1-(pyridin-2-yldiazenyl)naphthalen-2-ol,
4,4'-1,3-phenylenebis(diazene-2,1-diyl)dibenzene-1,3-diamine,
N-ethyl-1-((4-(-phenyldiazenyl)phenyl)diazenyl)naphthalen-2-amine,
4-((2,4-dinitrophenyl)diazenyl)-2-nitrophenol,
4-((4-aminophenyl)diazenyl)-N,N-dimethylaniline,
1,2-diphenyldiazene oxide,
1,2-diphenyldiazene,
4-((4-isothiocyanatophenyl)diazenyl)-N,N-dimethylaniline,
2-methyl-4-(o-tolyldiazenyl)aniline, 1-(4-ethoxy-3-methylphenyl)-2-p-tolyldiazene,
(3-((4-(phenylamino)phenyl)diazenyl)phenyl)sulfanolic acid,
4-(pyridin-2-yldiazenyl)benzene-1,3-diol,
4-((4-nitrophenyl)diazenyl)benzene-1,3-diol,
4-(thiazol-2-yldiazenyl)benzene-1,3-diol,
4-(phenyldiazenyl)benzene-1,3-diol,
4-((2,4-dihydroxyphenyl)diazenyl)benzenesulfonic acid,
4-((2,4-dihydroxyphenyl)diazenyl)-5-hydroxynaphthalene-2,7-disulfonic acid,
3-((2,4-dihydroxyphenyl)diazenyl)-4-hydroxybenzene-sulfonic acid,
2,4-dihydroxy-5-(m-tolyldiazenyl)benzaldehyde,
4-((1H-1,2,4-triazol-5-yl)diazenyl)benzene-1,3-diol,
4-methyl-6-(thiazol-2-yldiazenyl)benzene-1,3-diol,
5-methoxy-2-(thiazol-2-yldiazenyl)phenol,
5-methyl-4-((4-nitrophenyl)diazenyl)benzene-1,3-diol,
4-((2,5-dichlorophenyl)diazenyl)benzene-1,3-diol,
1-((4-nitrophenyl)diazenyl)naphthalen-2-ol,
N,N-dimethyl-4-(phenyldiazenyl)aniline,
5-methyl-4-(thiazol-2-yldiazenyl)benzene-1,3-diol,
1-(4-nitrophenyl)-3-(4-(phenyldiazenyl)phenyl)triaz-1-ene,
or a physiologically acceptable salt thereof.

8. The compound according to any one of the previous items which comprises at least one detectable group.

9. The compound according to any one of the previous items, which comprises at least one deuterium atom which is particularly a substituent of X or Y or a substituent of a group —NH$_2$ or —NHR$_1$.

10. The compound according to any one of the previous items which comprises at least one $^{18}$F or $^{19}$F atom which is particularly a substituent selected from an $^{18}$F or $^{19}$F atom or a group comprising an $^{18}$F or $^{19}$F atom.

11. The compound according to any one of the previous items for use as an inhibitor of amyloid-β aggregate formation and/or as a modulator of amyloid surface properties, and/or as an activator of degradation or reduction of amyloid-β aggregates.

12. The compound for use according to any of the previous items in the treatment, diagnosis and/or monitoring of a disease associated with, accompanied by and/or caused by protein misfolding or formation of protein aggregates.

13. The compound for use according to item 12, wherein the disease is selected from Alzheimer's disease, Parkinson's disease, an amyloidosis such as αβ-amyloidosis, primary systemic amyloidosis, secondary systemic amyloidosis, senile systemic amyloidosis, familial amyloid polyneuropathy 1, hereditary cerebral amyloid angiopathy, hemodialysis-related amyloidosis, familial amyloid polyneuropathy III, Finnish hereditary systemic amyloidosis, type 2 diabetes, medullary carcinoma of thyroid, atrial amyloidosis, hereditary non-neuropathic systemic amyloidosis, injection-localized amyloidosis, hereditary renal amyloidosis, amyotrophic lateral sclerosis, schizophrenia, sickle cell anaemia, unstable haemoglobin inclusion body haemolysis, α1-antitrypsin deficiency, antithrombin deficiency, thromboembolic disease, spinobulbar muscular atrophy (Kennedy disease), Huntington's disease, dentatorubral-pallidoluysian atrophy (Haw River syndrome), spinocerebellar ataxia type 1, spinocerebellar ataxia type 2, spinocerebellar ataxia type 3 (Machado-Joseph disease), spinocerebellar ataxia type 6, spinocerebellar ataxia type 7, spinocerebellar ataxia type 17, transmissible spongiform encephalopathies (prion diseases): Bovine spongiform encephalopathy, kuru, Gerstmann-Straeussler-Scheinker syndrome, fatal familial insomnia, scrapie, Creutzfeldt-Jakob disease and variant Creutzfeldt-Jakob disease, wherein the disease particularly is an amyloidosis, in particular αβ-amyloidosis.

14. A pharmaceutical and/or diagnostic composition comprising at least one compound of formula I as defined in any one of items 1-10 and optionally a physiologically acceptable carrier.

15. A method for the treatment or diagnosis of a disease associated with, accompanied by and/or caused by protein misfolding or formation of protein aggregates, comprising administering a subject in need thereof a pharmaceutically or diagnostically effective amount of a compound according to any one of items 1-10, wherein the subject is particularly a human patient.

16. Use of a compound of formula I as an inhibitor of protein misfolding and/or the accumulation of a misfolded protein or protein aggregate, and/or as a modulator of amyloid surface properties, and/or as an activator of degradation of a misfolded protein or a protein aggregate.

The invention claimed is:

1. A method for inhibiting or reducing amyloid-β-aggregate formation, comprising administering to a human subject in need thereof a compound of formula (I),

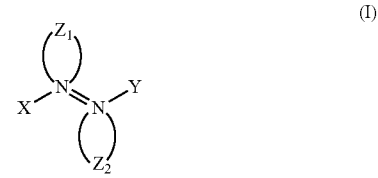

or a physiologically acceptable salt or tautomer, thereof, wherein
X is phenyl which is substituted with at least one first substituent different from H, and optionally at least one further substituent different from H,
  wherein the first substituent is selected from the group consisting of —NHR$_1$, and —N(R$_1$)$_2$,
Y is a 5- or 6-membered aromatic or heteroaromatic radical,
Z$_1$ and Z$_2$ are free electron pairs or one of Z$_1$ and Z$_2$ is =O and the other a free electron pair, and
R$_1$ is phenyl,
with the proviso that when at least one of X and Y is substituted by at least one group selected from —COOH and —SO$_3$H, at least one of X and Y is substituted with at least one group selected from the group consisting of —NH$_2$, —NHR$_1$ and —N(R$_1$)$_2$, in an amount sufficient to inhibit or reduce amyloid-β-aggregate formation.

2. The method according to claim 1, wherein X is substituted with at least one further substituent different from H, Y is substituted with at least one substituent different from H, and R$_1$ is substituted with at least one substituent different from H.

3. The method of claim 1, wherein in the compound of formula (I) administered to said subject, neither X nor Y is substituted with a —COOH group.

4. The method of claim 1, wherein in the compound of formula (I) administered to said subject, X is selected from the group consisting of
(i) phenyl substituted with at least one first substituent on position 4, on positions 2 and 4 or on positions 2, 4 and 5, and (ii) phenyl substituted with a) a group —NH$_2$, —NHR$_1$ or N(R$_1$)$_2$ on position 4, or on positions 2 and 4, b) a group —OH on position 4 or on positions 2 and 4, c) a group —NO$_2$ on position 2 or positions 2 and 4, or d) a group —NCS on position 2.

5. The method of claim 1, wherein in the compound of formula (I) administered to said subject, Y is selected from the group consisting of phenyl, pyridyl, thiazolyl and triazolyl.

6. The method of claim 5, wherein in the compound of formula (I) administered to said subject, Y is selected from the group consisting of pyrid-1-yl, pyrid-2-yl, pyrid-3-yl, pyrid-4-yl, 1,3-thiazolyl, 1,3-thiazol-2-yl, 1,2,4-triazolyl and 1,2,4-triazol-5-yl.

7. The method of claim 5, wherein Y is unsubstituted or substituted with at least one substituent which is selected from the group consisting of —NH$_2$, —NH(C$_{1-6}$ alkyl), —N(C$_{1-6}$ alkyl)$_2$, —OH, —NO$_2$ and halo.

8. The method according to claim 1, wherein the compound of formula (I) administered to said subject, is selected from the group consisting of
N-phenyl-4-(phenyldiazenyl)aniline,
4-((4-nitrophenyl)diazenyl)-N-phenylaniline,
(3-((4-(phenylamino)phenyl)diazenyl)phenyl)sulfonic acid, and
4-((4-aminophenyl)diazenyl)-N-phenylaniline,
or a physiologically acceptable salt thereof.

9. A method for the diagnosis of amyloid-β-aggregate formation in a human subject, comprising administering to a human subject suspected of having amyloid-β-aggregate formation, a diagnostically effective amount of compound of formula (I),

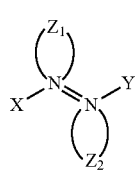
(I)

or a physiologically acceptable salt or tautomer thereof, wherein
X is phenyl which is substituted with at least one first substituent different from H, and optionally at least one further substituent different from H,
wherein the first substituent is selected from the group consisting of —NHR$_1$, and —N(R$_1$)$_2$,
Y is a 5- or 6-membered aromatic or heteroaromatic radical,
Z$_1$ and Z$_2$ are free electron pairs or one of Z$_1$ and Z$_2$ is =O and the other a free electron pair, and
R$_1$ is phenyl,
with the proviso that when at least one of X and Y is substituted by at least one group selected from —COOH and —SO$_3$H, at least one of X and Y is substituted with at least one group selected from the group consisting of —NH$_2$, —NHR$_1$ and —N(R$_1$)$_2$,
wherein the compound of formula (I) administered to said subject is labelled with at least one radioactive or non-radioactive detectable group as a substituent of X or Y or a substituent of a group NH$_2$ or NHR$_1$, and detecting said detectable group as an indication of the presence of amyloid-β-aggregates.

10. The method according to claim 1, wherein at least one hydrogen in a substituent of X or Y or a substituent of a group —NH$_2$ or —NHR$_1$ is replaced by a deuterium atom.

11. The method according to claim 1, wherein the compound of formula (I) administered to said subject has at least one $^{18}$F or $^{19}$F atom or a group comprising an $^{18}$F or $^{19}$F atom as a substituent of X or Y or a substituent of a group NH$_2$ or NHR$_1$.

12. The method according to claim 1, wherein the compound of formula (I) administered to said subject is an inhibitor of amyloid-β aggregate formation, a modulator of amyloid surface properties, and/or an activator of degradation or reduction of amyloid-β aggregates.

13. The method according to claim 1, wherein said human subject is suffering from a disease selected from the group consisting of Alzheimer's disease, Parkinson's disease, αβ-amyloidosis, primary systemic amyloidosis, secondary systemic amyloidosis, senile systemic amyloidosis, familial amyloid polyneuropathy 1, hereditary cerebral amyloid angiopathy, hemodialysis-related amyloidosis, familial amyloid polyneuropathy III, Finnish hereditary systemic amyloidosis, type 2 diabetes, medullary carcinoma of thyroid, atrial amyloidosis, hereditary non-neuropathic systemic amyloidosis, injection-localized amyloidosis, hereditary renal amyloidosis, amyotrophic lateral sclerosis, schizophrenia, sickle cell anaemia, unstable haemoglobin inclusion body haemolysis, α1-antitrypsin deficiency, antithrombin deficiency, thromboembolic disease, spinobulbar muscular atrophy (Kennedy disease), Huntington's disease, dentatorubral-pallidoluysian atrophy (Haw River syndrome), spinocerebellar ataxia type 1, spinocerebellar ataxia type 2, spinocerebellar ataxia type 3 (Machado-Joseph disease), spinocerebellar ataxia type 6, spinocerebellar ataxia type 7, spinocerebellar ataxia type 17, and transmissible spongiform encephalopathies (prion diseases).

14. The method according to claim 13, wherein said transmissible spongiform encephalopathies are selected from the group consisting of Bovine spongiform encephalopathy, kuru, Gerstmann-Straeussler-Scheinker syndrome, fatal familial insomnia, scrapie, Creutzfeldt-Jakob disease and variant Creutzfeldt-Jakob disease.

15. The method according to claim 13, wherein said disease is an amyloidosis.

16. The method according to claim 15, wherein said amyloidosis is αβ-amyloidosis.

17. A method for inhibiting amyloid-β aggregate formation, inhibiting the accumulation of amyloid-β aggregate, modulating amyloid surface properties, and/or activating degradation of an amyloid-β aggregate, comprising administering a compound of formula (I) to a subject,

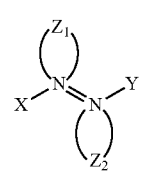
(I)

or a physiologically acceptable salt or tautomer, thereof, wherein
X is phenyl which is substituted with at least one first substituent different from H, and optionally at least one further substituent different from H,
wherein the first substituent is selected from the group consisting of —NHR$_1$, and —N(R$_1$)$_2$,
Y is a 5- or 6-membered aromatic or heteroaromatic radical, $Z_1$ and $Z_2$ are free electron pairs or one of $Z_1$ and $Z_2$ is =O and the other a free electron pair, and $R_1$ is phenyl, with the proviso that when at least one of X and Y is substituted by at least one group selected from —COOH and —SO$_3$H, at least one of X and Y is substituted with at least one group selected from the group consisting of —NH$_2$, —NHR$_1$ and —N(R$_1$)$_2$, in an amount sufficient to inhibit amyloid-β aggregate formation, inhibit the accumulation of amyloid-β aggregate, modulate amyloid surface properties, and/or activate degradation of an amyloid-β aggregate.

18. The method according to claim 9, wherein said at least one radioactive detectable group includes an isotope of I, Br or F.

19. The method according to claim 18, wherein said radioactive detectable group is an isotope selected from the group consisting of $^{123}$I, $^{125}$I, $^{131}$I, $^{75}$Br, $^{76}$Br, $^{77}$Br, $^{18}$F and $^{19}$F.

20. The method according to claim 19, wherein said radioactive detectable group is selected from the group consisting of —CH$_2$—$^{18}$F, —CH$_2$—$^{19}$F, —CH($^{18}$F)$_2$, —CH($^{19}$F)$_2$, —C$^{18}$F$_3$, —C($^{19}$F)$_3$, —CH$_2$—CH$_2$—$^{18}$F, ($^{19}$F), O—CH$_2$—$^{18}$F, ($^{19}$F) O—CH$_2$—CH$_2$—$^{18}$F, CH$_2$—CH$_2$—CH$_2$—$^{18}$F, O—CH$_2$—CH$_2$—CH$_2$—$^{18}$F, and aromatic compounds with one to four $^{18}$F or $^{19}$F groups.

* * * * *